United States Patent [19]

Shannon et al.

[11] Patent Number: 5,945,416
[45] Date of Patent: Aug. 31, 1999

[54] METHOD FOR TREATING PAIN

[75] Inventors: Harlan E. Shannon, Carmel, Ind.; Daniel E. Womer, Thornton, Colo.

[73] Assignee: Eli Lilly and Company, Indianapolis, Ind.

[21] Appl. No.: 08/823,461

[22] Filed: Mar. 24, 1997

Related U.S. Application Data

[60] Provisional application No. 60/014,130, Mar. 25, 1996, provisional application No. 60/014,132, Mar. 25, 1996, provisional application No. 60/014,128, Mar. 25, 1996, and provisional application No. 60/014,129, Mar. 25, 1996.

[51] Int. Cl.$^6$ .................................................... A61K 31/55
[52] U.S. Cl. ............................................................ 514/220
[58] Field of Search ................................................ 514/220

[56] References Cited

U.S. PATENT DOCUMENTS 5,229,382  7/1993  Chakrabarti et al. ................. 514/220
5,605,897  2/1997  Beasley, Jr. et al. ................. 514/220

*Primary Examiner*—Theodore J. Criares
*Attorney, Agent, or Firm*—Arleen Palmberg; Macharri Vorndram-Jones

[57] ABSTRACT

The present invention provides a method for treating pain using a composition comprising olanzapine and Drug Useful in the Treatment of Pain.

44 Claims, No Drawings

METHOD FOR TREATING PAIN

This application claims the benefit of U.S. provisional application No. 60/014,130, filed Mar. 25, 1996, U.S. provisional application No. 60/014,132, filed Mar. 25, 1996, U.S. provisional application No. 60/014,128, filed Mar. 25, 1996, and U.S. Provisional Application No. 60/014,129, filed Mar. 25, 1996.

FIELD OF THE INVENTION

This invention provides a method for treating pain comprising administering 2-methyl-4-(4-methyl-1-piperazinyl)-10H-thieno[2,3-b][1,5] benzodiazepine, (hereinafter referred as "olanzapine") and Drug Useful in the Treatment of Pain to an animal in need of such treatment.

BACKGROUND OF THE INVENTION

This invention relates to a therapeutic combination of compounds to provide analgesic activity.

Surprisingly, we have discovered that olanzapine can be particularly useful for treating pain when used in combination with a Drug Useful in the Treatment of Pain. More specifically, the invention provides a method of synergistically treating pain in an animal using olanzapine in combination with a Drug Useful in the Treatment of Pain to provide a synergistic effect.

There are many Drugs Useful for the Treatment of Pain which are known in the literature and to the skilled artisan. Oral combinations of aspirin with codeine or other narcotic analgesics are known to provide additive analgesic effects in man. The Pharmacological Basis of Therapeutics, 5th edition, Macmillan Publishing Co., 1975, pp 325–358.

More active analgesic combinations are in constant demand because they offer the attractive possibility of relieving pain with reduced dosages, thereby diminishing the expected side effects and toxicity that would otherwise result from higher dosages. It would be particularly desirable to acquire a synergistic combination effect. Such a composition is the subject of the present invention.

It is known that olanzapine can provide antipsychotic activity and is now commercially available for the treatment of psychosis. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. Surprisingly, and in accordance with this invention, Applicants have discovered that olanzapine can be useful for the treatment of pain and can provide a synergistic effect when administered with one or more Drugs Useful in the Treatment of Pain. Olanzapine could address a long felt need for a safe and effective treatment for pain.

SUMMARY OF THE INVENTION

The present invention provides a method for treating pain comprising administering to a patient in need thereof, an analgesic composition comprising olanzapine or a pharmaceutically acceptable salt thereof; and one or more Drugs Useful in the Treatment of Pain in a weight ratio of olanzapine to Drug Useful in the Treatment of Pain of from about one (1) part olanzapine to about one (1) to about one thousand (1000) parts Drug Useful in the Treatment of Pain.

A preferred composition is a weight ratio of olanzapine to Drug Useful in the Treatment of Pain of about one (1) part olanzapine to about one (1) to about hundred (100) parts Drug Useful in the Treatment of Pain. An especially preferred ratio is about one part olanzapine (1) to from about one (1) to about thirty (30) parts Drug Useful in the Treatment of Pain. A further preferred ratio may be about one part olanzapine to from about one (1) to about ten (10) parts Drug Useful in the Treatment of Pain. A final preferred ratio may be about one (1) part olanzapine to about one (1) to about three (3) parts Drug Useful in the Treatment of Pain.

One preferred group of Drugs Useful in the Treatment of Pain are Non-Steroidal Antiinflammatory Agents (hereinafter "NSAIDS") and include, but are in no way limited to salicylates such as aspirin. Another preferred group of NSAIDS include, but are not limited to, indomethacin, ibuprofen, naproxen, fenoprofen, tolmetin, sulindac, meclofenamate, ketoprofen, piroxicam, flurbiprofen, and diclofenac.

Particularly preferred NSAIDS are selected from the group consisting of ibuprofen and naproxen. Another particularly preferred NSAIDS is aspirin.

The invention further provides a composition for treating pain comprising olanzapine or a pharmaceutically acceptable salt or solvate thereof and one or more Drug Useful in the Treatment of Pain in a weight ratio of olanzapine to Drug Useful in the Treatment of Pain of about one part olanzapine to from about one (1) to about one thousand (1000) parts Drug Useful in the Treatment of Pain.

DETAILED DESCRIPTION OF THE INVENTION

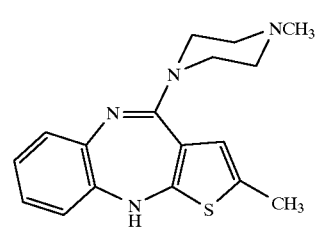

(I)

or an acid addition salt thereof.

It is especially preferred that olanzapine will be the Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |

-continued

| d |
|---|
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper $K_a$ radiation source of wavelength, $1 = 1.541$ Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II will preferably contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and $I/I_1$ represents the typical relative intensities:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper $K_a$ of wavelength $1=1.541$ Å. The interplanar spacings in the column marked "d" are in Angstroms. The typical relative intensities are in the column marked "I/I$_1$".

As used herein, the term "Drug Useful in the Treatment of Pain" shall mean a compound, or a pharmaceutically acceptable salt thereof, that is known to the artisan to have clinical analgesic activity. As used herein, Drug Useful in the Treatment of Pain shall include, but is in no way limited to, NSAIDS, opioid compounds, and alpha adrenergic compounds.

Drugs Useful in the Treatment of Pain shall also encompass classical analgesic agents known to the artisan. See for example, Goodman and Gillman, The Pharmacological Basis of Therapeutics, 5$^{th}$ edition, Macmillan Publishing Co., 1975, pp 325–358, and similar references commonly consulted by the skilled artisan. Thus, the term shall include, for example, Tylenol #3, tricyclic antidepressants (for example desipramine, imipramine, amytriptiline, nortriptiline), anticonvulsants (for example, carbamazepine, gatapentine, valproate), and serotonin reuptake inhibitors (for example, fluoxetine, paroxetine, citalopram, sertraline), mixed serotonin-norepinephrine reuptake inhibitors (for example venlafaxine, duloxetine), serotonin receptor agonists and antagonists, cholinergic (muscarinic and nicotinic) analgesics, and neurokinin antagonists.

Especially preferred Drugs Useful in the Treatment of Pain can be selected from the group consisting of tricyclic antidepressants, anticonvulsants, and serotonin-norepinephrine reuptake inhibitors.

The term "alpha-adrenergic compounds", as used herein, represents a compound having central alpha-adrenergic receptor activity. The most preferred central alpha-adrenergic active compound is clonidine or a pharmaceutically acceptable salt thereof having the chemical name: 2-(2,6-dichlorophenylamino)-2-imidazoline. New alpha adrenergic active agents are undergoing pharmacolgoical development. The present invention encompasses all such agents which function as a central alpha-adrenergic active compound.

Clonidine is known to be useful for treating hypertension. see Physicians' Desk Reference, 45th Ed. (1991) p. 673.

The term "opioids" or "opioid compounds", as used herein, has the meaning commonly associated with the term by the skilled artisan. Preferred opioid compounds are selected from the group consisting of morphine, codeine, meperidine, methadone, propoxyphene, levorphanol, hydromorphone, oxymorphone, oxycodone, brompton's cocktail, pentazocine, butorphanol, nabuphine, and buprenorphine.

The term "NSAIDS", as used herein, represents a non-steroidal anti-inflammatory drug which can be identified as such by the skilled artisan. For example, the Merck Manual, 16th Edition, Merck Research Laboratories (1990) pp 1308–1309 provide well known examples of NSAIDS. The term is intended to include, but is not limited to salicylates such as aspirin. Further, the term includes, but is not limited to, indomethacin, ibuprofen, naproxen, fenoprofen, tolmetin, sulindac, meclofenamate, ketoprofen, piroxicam, flurbiprofen, and diclofenac. Especially preferred NSAIDS include ibuprofen, and naproxen. Another especially preferred NSAID is aspirin. Particularly preferred NSAIDS include aspirin and ibuprofen. The salicylates may include acetylsalicylic acid, sodium acetylsalicylic acid, calcium acetylsalicylic acid, salicylic acid, and sodium salicylate. The term NSAIDS shall refer to any compound acting as a non-steroidal antiinflammatory agent. Applicants appreciate that new NSAIDS may be in development, and the present invention contemplates a synergistic composition comprising such new agents with olanzapine as well.

As used herein, the term "animal" shall refer to a vertebrate animal. Most preferably, the vertebrate animal is a mammal. As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

In the composition of this invention olanzapine or a pharmaceutically acceptable salt thereof and one or more Drug Useful in the Treatment of Pain are combined in a weight ratio of olanzapine to Drug Useful in the Treatment of Pain of about one (1) to about one (1) to about one thousand (1000) parts Drug Useful in the Treatment of Pain.

A preferred composition is a weight ratio of olanzapine to Drug Useful in the Treatment of Pain of about one (1) part olanzapine to from about one (1) to about one hundred (100) parts Drug Useful in the Treatment of Pain. An especially preferred ratio is about one part olanzapine to from about one (1) to about thirty (30) parts Drug Useful in the Treatment of Pain. A further preferred ratio may be about one part olanzapine to about one (1) to about ten (10) parts Drug Useful in the Treatment of Pain. A final preferred ratio may be about one (1) part olanzapine to from about one (1) to about three (3) parts Drug Useful in the Treatment of Pain.

Olanzapine is effective over a wide dosage range; however, it is desirable to administer a dosage that is as low as possible. The amount of Drug Useful in the Treatment of Pain present in the composition is adjusted as described above in ratio to the olanzapine dosage. For example, dosages per day of the olanzapine will normally fall within the range of about 0.1 mg to about 30 mg per day and the Drug Useful in the Treatment of Pain in the composition would be from about 3 to about 1000 times this amount. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from pain, the compounds may also be administered by a variety of other routes such as the transdermal, parenteral, subcutaneous, intranasal, intramuscular and intravenous routes. Such formulations may be designed to provide delayed or controlled release using formulation techniques which are known in the art.

As used herein the term "treating" includes prophylaxis of a physical and/or mental condition or amelioration or elimination of the developed condition once it has been established or alleviation of the characteristic symptoms of such condition.

As used herein the term "pain" shall refer to all types of pain. Preferably, the term shall refer to chronic pains, such as neuropathic pain, and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferredly refer to nociceptive pain or nociception.

The results of pharmacological studies show that olanzapine has muscarinic cholinergic receptor activity. The compound is active at the dopamine D-1 and D-2 receptors as indicated by an IC50 of less than 1 μM in the 3H-SCH233390 (Billard, et al. Life Sciences 35: 1885 (1984)) and the 3H spiperone (Seeman et al Nature 216: 717 (1976)) binding assays respectively. Further, olanzapine is active at the 5-HT-2 receptor and 5-HT1C receptor. The complex pharmacological profile of the compound provides a medicament which can be useful for the treatment of pain.

The dosage administered will, of course, vary depending on known factors such as the pharmacodynamic characteristics of the particular agent, and its mode and route of administration; age, health, and weight of the recipient; nature and extent of the symptoms, kind of concurrent treatment, frequency of treatment, and the effect desired. Usually, the daily dosage can be such that the active ingredient is administered at a daily dosage of from about 0.2 mg to about 30 mg olanzapine and from about 0.6 to about 200 mg/kg of Drug Useful in the Treatment of Pain.

As used herein the term "parts", with reference to the composition, shall refer to parts by weight in the composition in proportion to the Drug Useful in the Treatment of Pain or olanzapine, as the case may be.

Compositions suitable for internal administration contain from about one half (0.5) milligrams to about 600 milligrams of active ingredient per unit. In these pharmaceutical compositions, the active ingredient will ordinarily be present in an amount of from about 0.5% to about 95% by weight based on the total weight of the composition.

Typical compositions include olanzapine or a pharmaceutically acceptable acid addition salt thereof and one or more Drug Useful in the Treatment of Pain, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredients after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the composition is dispensed in unit form comprising from about 1 mg to about 30 mg in a pharmaceutically acceptable carrier per unit dosage.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The compositions of this invention may be suitable for administration to an animal. Such animals include both domestic animals, for example livestock, laboratory animals, and household pets, and non-domestic animals such as wildlife. More preferably, the animal is a vertebrate. Most preferably, a compound of this invention shall be administered to a mammal. It is especially preferred that the animal is a domestic mammal or a human. For such purposes, a compound of this invention may be administered as a feed additive.

The most preferred mammal is a human.

Utility Test Methods

The unexpectedly enhanced analgesic activity of the composition of the invention is evidenced by tests initially conducted on mice. Mice weighing from about 18–25 grams at the time of testing are used for the following studies. All mice are dosed by the oral route with olanzapine and/or Drug Useful in the Treatment of Pain.

Mouse Writhing Test

An accepted standard for detecting and comparing the analgesic activity of different classes of analgesic compounds for which there is a good correlation with human analgesic activity is the prevention of acetic acid induced writhing in mice [R. Koster et al. Acetic acid for analgesic screening. *Fed. Proc.* 18: 412, 1959].

Mice, treated with various doses of olanzapine, Drug Useful in the Treatment of Pain, olanzapine:Drug Useful in the Treatment of Pain combinations, or vehicle are injected intraperitoneally with a standard challenge dose of acetic acid 5 minutes prior to a designated observation period. The acetic acid is prepared as a 0.55% solution and injected at a volume of 0.1 ml/10 grams of body weight. For scoring purposes a "writhe" is indicated by whole body stretching or contracting of the abdomen during an observation period beginning about five minutes after the administration of acetic acid.

Sciatic Nerve Ligation Model

An accepted model for assessment of neuropathic pain analgesia is the sciatic nerve ligation model [Bennett, G. J. and Xie, Y.-K. A peripheral mononeuropathy in rat that produces disorders of pain sensation like those seen in man. Pain 33 (1988) 87–107; Lee, Y.-W., Chaplan, S. R. and Yaksh, T. L.: Systemic and supraspinal, but not spinal, opiates suppress allodynia in a rat neuropathic pain model. Neuroci Lett 186 (1995) 111–114]. Rats are anesthetized and a nerve ligation procedure performed. The common sciatic nerve is exposed and 4 ligatures tied loosely around it with about 1 mm spacing. One day to 10 weeks after surgery, the nociceptive testing is performed. Responses to noxious heat are determined by placing the rats in a chamber with a clear glass floor and aiming at the plant surface of the affected foot a radiant heat source from beneath the floor. Increased latency to withdraw the hindpaw is demonstrative of analgesic activity. Responses to normally innocuous mechanical stimuli is determined by placing the rats in a chamber with a screen floor and stimulating the plant surface of the hind paw with graduated von Frey hairs which are calibrated by the grams of force required to bend them. Rats with sciatic nerve ligation respond to lower grams of mechanical stimulation by reflexive withdrawal of the foot than unoperated rats. This response to stimuli which are normally innocuous is termed allodynia. Increases in the grams of mechanical force required to produce foot withdrawal is demonstrative of antiallodynic activity.

Formalin Test

The formalin test is a well accepted model of inflammatory [Malmberg, A. B. and Yaksh, T. L.: Antinociceptive actions of spinal nonsteroidal anti-inflammatory agents on the formalin test in the rat. The Journal of Pharmacology and Experimental Therapeutics 263 (1992) 136–146]. Rats are anesthetized and when there is a loss of spontaneous movement they are injected subcutaneously in the dorsal surface of the hindpaw with 50 µl of 5% formalin solution using a 30 gauge needle. Rats are then individually placed in an open Plexiglas chamber for observation, and within a maximum interval of 1 to 2 min, the animals display recovery from anesthesia with spontaneous activity and normal motor function. Pain behavior is quantified by periodically counting the incidents of spontaneous flinching/shaking of the injected paw. The flinches are counted for 1-min periods at 1- to 2-, 5- to to 6- and 5 min intervals during the interval from 10 to 60 min. Inhibition of the pain behavior is demonstrative of an analgesic activity.

All $ED_{50}$ values and their standard errors of the mean (S.E.M.) are determined using accepted numerical methods. For example, see R. E. Kirk (1982) Experimental Design: Procedures for the behavioral sciences, 2nd ed. Belmont, Calif.: Brooks/Cole Publishing Co. The interaction of the dosages on analgesia in mice or rats is demonstrated graphically by the Loewe isobologram (S. Loewe, Pharm. Rev. 9: 237–242, 1957).

The interaction of olanzapine and Drug Useful in the Treatment of Pain on analgesia in mice is demonstrated by Loewe isobologram analysis. In the isobolographic analysis, the analgesic effects of olanzapine are presented on the X-axis and of the other compound used in the treatment of pain on the Y-axis. The line connecting the $ED_{50}$ dosages of olanzapine alone and Drug Useful in the Treatment of Pain alone represents the "ED50 addition line" which indicates the expected location of the $ED_5$ values for olanzapine and Drug Useful in the Treatment of Pain combinations if simple additivity were to describe their combined effects. According to Loewe's isobolographic theory, if the analgesic effects of olanzapine and an Drug Useful in the Treatment of Pain were simply additive to one another, the expected location of the $ED_{50}$ values of the olanzapine and Drug Useful in the Treatment of Pain components of each fixed dosage ratio would lie on the addition line. Combination ED50 values located significantly below the $ED_{50}$ addition line would represent unexpectedly enhanced analgesic activity and combination $ED_{50}$ values located above the line would represent unexpected diminished analgesic effect.

One method to establish the significance of such unexpected enhanced or diminished activity is to calculate the SEM values for each $ED_{50}$. If the SEM values do not overlap the line of addition, then the ED50 values are significantly different from the line of addition.

Surprisingly, such experiments demonstrate that compositions comprised of olanzapine and Drug Useful in the Treatment of Pain show a statistically significant synergistic analgesic effect.

For example, morphine and olanzapine at a ratio of one part olanzapine to ten parts morphine and at a ratio of one part olanzapine to thirty parts morphine showed statistically significant analgesic effect in the mouse writhe test. Similar results were obtained for the combination of olanzapine and diclofenac, olanzapine and ibuprofen, and olanzapine and acetaminophen for a range of ratios.

It will be apparent that the instant specifications and examples are set forth by way of illustration and not limitation, and that various modifications and changes may be made without departing from the spirit and scope of the present invention.

Surprisingly, such experiments demonstrate that compositions comprised of olanzapine and one or more Drug Useful in the Treatment of Pain provides a statistically significant synergistic analgesic effect.

Clinical Observations

A double-blind multicenter clinical trial is designed to assess the safety and efficacy of olanzapine. Patients are randomized to olanzapine, composition of this invention, Drug Useful in the Treatment of Pain alone, or placebo. Patients are monitored for perception of pain using standard methods.

The materials for the present invention can be purchased or prepared by a variety of procedures well known to those of ordinary skill in the art. Olanzapine can be prepared as described by Chakrabarti in U.S. Pat. No 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

Preparation 1

Technical Grade olanzapine

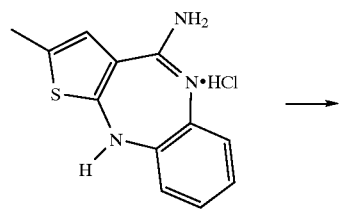

Intermediate 1

-continued

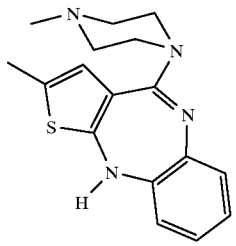

In a suitable three neck flask the following was added:

Dimethylsulfoxide (analytical): 6 volumes
Intermediate 1: 75 g
N-Methylpiperazine (reagent): 6 equivalents Intermediate 1 can be prepared using methods known to the skilled artisan. For example, the preparation of the Intermediate 1 is taught in the '382 patent. A sub-surface nitrogen sparge line was added to remove the ammonia formed during the reaction. The reaction was heated to 120° C. and maintained at that temperature throughout the duration of the reaction. The reactions were followed by HPLC until ² 5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

Preparation 2

Form II olanzapine polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency $\leq 97\%$, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), ibuprofen (3% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A composition for treating pain comprising olanzapine or a pharmaceutically acceptable salt or solvate thereof; and one or more Drug Useful in the Treatment of Pain in a weight ratio of from about one part olanzapine to from about one (1) part to about one thousand (1000) parts Drug Useful in the Treatment of Pain.

2. A composition of claim 1 wherein the Drug Useful in the Treatment of Pain is an NSAIDS.

3. A composition of claim 2 wherein the NSAIDS is selected from the group consisting of aspirin, indomethacin, ibuprofen, naproxen, fenoprofen, tolmetin, sulindac, meclofenamate, keoprofen, piroxicam, flurbiprofen, and diclofenac or a pharmaceutically acceptable salt thereof.

4. A composition of claim 1 wherein olanzapine is Form II olanzapine polymorph having a typical x-ray diffraction pattern as follows, wherein d represents the interplanar spacing:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |

| d |
|---|
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

5. A composition of claim 4 wherein the Drug Useful in the Treatment of Pain is selected from the group consisting of aspirin, ibuprofen, and naproxen.

6. A composition of claim 1 wherein the weight ratio of olanzapine to Drug Useful in the Treatment of Pain is from about one part olanzapine to from about one (1) to about one hundred (100) parts Drug Useful in the Treatment of Pain.

7. A composition of claim 6 wherein the weight ratio is from about one part olanzapine to from about one (1) to about thirty (30) parts Drug Useful in the Treatment of Pain.

8. A composition of claim 7 wherein the weight ratio is from about one part olanzapine to from about one (1) to about ten (10) parts Drug Useful in the Treatment of Pain.

9. A composition of claim 8 wherein the Drug Useful in the Treatment of Pain is selected from the group consisting of morphine, acetaminophen, ibuprofen, and diclofenac.

10. A composition of claim 1 wherein the Drug Useful in the Treatment of Pain is an opioid compound.

11. A composition of claim 4 wherein the Drug Useful in the Treatment of Pain is an opioid compound.

12. A composition of claim 7 wherein the Drug Useful in the Treatment of Pain is an opioid compound.

13. A composition of claim 10 wherein the opioid compound is selected from the group consisting of morphine, codeine, meperidine, methadone, propoxyphene, levorphanol, hydromorphone, oxymorphone, oxycodone, brompton's cocktail, pentazocine, butorphanol, nabuphine, and buprenorphine.

14. A composition of claim 13 wherein the opioid compound is selected from the group consisting of morphine, oxymorphine, oxycodone, hydromorphine, codeine, and methadone.

15. A composition of claim 1 wherein the Drug Useful in the Treatment of Pain is selected from the group consisting of Tylenol #3, tricyclic antidepressants (for example desipramine, imipramine, amytriptiline, nortriptiline), anti-convulsants (for example, carbamazepine, gatapentine, valproate), and serotonin reuptake inhibitors (for example, fluoxetine, paroxetine, citalopram, sertraline), mixed serotonin-norepinephrine reuptake inhibitors (for example venlafaxine, duloxetine), serotonin receptor agonists and antagonists, cholinergic (muscarinic and nicotinic) analgesics, and neurokinin antagonists.

16. A composition of claim 4 wherein the Drug Useful in the Treatment of Pain is selected from the group consisting of Tylenol #3, tricyclic antidepressants, anticonvulsants, and serotonin reuptake inhibitors, mixed serotonin-norepinephrine reuptake inhibitors analgesics, and neurokinin antagonists.

17. A composition of claim 16 wherein the Drug Useful in the Treatment of Pain is a tricyclic antidepressant.

18. A composition of claim 1 wherein the Drug Useful in the Treatment of Pain is an alpha adrenergic compound.

19. A composition of claim 18 central alpha-adrenergic active compound is Clonidine or a pharmaceutically acceptable salt thereof.

20. A composition of claim 4 wherein the Drug Useful in the Treatment of Pain is an alpha adrenergic compound.

21. A composition of claim 7 wherein the Drug Useful in the Treatment of Pain is an alpha adrenergic compound.

22. A composition of claim 1 wherein the composition can provide a synergistic analgesic effect.

23. A composition for treating pain comprising olanzapine, or a pharmaceutically acceptable salt or solvate thereof, and ibuprofen, or a pharmaceutically acceptable salt thereof, in a weight ratio of about one part olanzapine to from about one (1) to about one thousand (1000) parts ibuprofen.

24. A composition of claim 23 wherein the olanzapine is Form II olanzapine polymorph.

25. A composition of claim 23 wherein the weight ratio is about one part olanzapine to from about one (1) to about one hundred (100) parts ibuprofen.

26. A composition of claim 23 wherein the weight ratio is about one part olanzapine to from about one (1) to about thirty (30) parts ibuprofen.

27. A composition of claim 26 wherein the weight ratio is about one part olanzapine to from about one (1) to about ten (10) parts ibuprofen.

28. A method for treating pain comprising administering an analgesic dose of a composition comprising olanzapine or a pharmaceutically acceptable salt or solvate thereof; and one or more Drug Useful in the Treatment of Pain in a weight ratio of olanzapine to Drug Useful in the Treatment of Pain of from about one part olanzapine to from about one (1) to about one thousand (1000) parts Drug Useful in the Treatment of Pain.

29. A method of claim 28 wherein the Drug Useful in the Treatment of Pain is an NSAIDS.

30. A method of claim 28 wherein the weight ratio of olanzapine to Drug Useful in the Treatment of Pain is from about one (1) part olanzapine to from about one (1) to about one hundred (100) parts Drug Useful in the Treatment of Pain.

31. A method of claim 28 wherein the weight ratio of olanzapine to Drug Useful in the Treatment of Pain is from about one (1) part olanzapine to from about one (1) to about thirty (30) parts Drug Useful in the Treatment of Pain.

32. A method of claim 28 wherein olanzapine is Form II olanzapine polymorph having a typical x-ray diffraction pattern as follows, wherein d represents the interplanar spacing:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |

-continued

| d |
|---|
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

33. A method of claim 28 wherein the Drug Useful in the Treatment of Pain is selected from the group consisting of alpha adrenergic compounds and opioid compounds.

34. A method of claim 28 wherein the Drug Useful in the Treatment of Pain is selected from the group consisting of Tylenol #3, tricyclic antidepressants, anticonvulsants, and serotonin reuptake inhibitors, mixed serotonin-norepinephrine reuptake inhibitors analgesics, and neurokinin antagonists.

35. A method of claim 28 wherein pain is neuropathic pain.

36. A method of claim 28 wherein pain is nociceptive pain.

37. A method of claim 28 wherein the pain is acute pain.

38. A method for treating pain comprising administering an analgesic dose of a composition comprising olanzapine, or a pharmaceutically acceptable salt or solvate thereof, and ibuprofen, or a pharmaceutically acceptable salt thereof, in a weight ratio of about one part olanzapine to from about one (1) to about one thousand (1000) parts ibuprofen.

39. A method of claim 38 wherein the olanzapine is Form II olanzapine polymorph.

40. A method of claim 38 wherein the weight ratio of olanzapine to ibuprofen is about one (1) part olanzapine to from about one (1) to about one hundred (100) parts ibuprofen.

41. A method of claim 40 wherein the weight ratio of olanzapine to ibuprofen is about one (1) part olanzapine to from about one (1) to about thirty (30) parts ibuprofen.

42. A method of claim 38 wherein the pain is neuropathic pain.

43. A method of claim 38 wherein the pain is nociceptive pain.

44. A method of claim 38 wherein the pain is acute pain.

* * * * *